United States Patent [19]
Kleiner et al.

[11] 3,965,148
[45] June 22, 1976

[54] PERFLUOROALKYL ALCOHOLS

[75] Inventors: Eduard K. Kleiner, New York; Robert A. Falk, New City, both of N.Y.

[73] Assignee: Ciba-Geigy Corporation, Ardsley, N.Y.

[22] Filed: May 5, 1975

[21] Appl. No.: 574,496

Related U.S. Application Data

[63] Continuation of Ser. No. 493,362, July 31, 1974, abandoned, which is a continuation of Ser. No. 281,084, Aug. 16, 1972, abandoned.

[52] U.S. Cl. .................. 260/481 R; 204/158 HE; 260/78.3 R; 260/78.3 UA; 260/455 R; 260/485 F; 260/561 S
[51] Int. Cl.² ..................................... C07C 149/20
[58] Field of Search ............................. 260/481 R

[56] References Cited
UNITED STATES PATENTS

| | | | |
|---|---|---|---|
| 3,172,910 | 3/1965 | Brace | 260/481 R |
| 3,706,789 | 12/1972 | Bonner | 260/481 R |

*Primary Examiner*—Vivian Garner
*Attorney, Agent, or Firm*—Joseph G. Kolodny; Edward McC. Roberts; Prabodh I. Almaula

[57] ABSTRACT

Perfluoroalkyl group containing alcohols are disclosed with utility as intermediates for the synthesis of oil and water repellent fluorochemicals. The alcohols are obtained by the addition of mercaptoalcohols to perfluoroalkyl group containing esters of fumaric, maleic, citraconic, mesaconic, itaconic, methylene malonic or aconitic acids.

6 Claims, No Drawings

PERFLUOROALKYL ALCOHOLS

This application is a continuation of application Ser. No. 493,362, filed July 31, 1974, now abandoned, which is a continuation of application Ser. No. 281,084, filed Aug. 16, 1972, now abandoned.

This invention is directed to novel perfluoroalkyl group containing alcohols. These alcohols are useful in the direct preparation of compounds which possess low free surface energies with oil and water repellancy.

The novel perfluoroalkyl group containing alcohols have the following general structure:

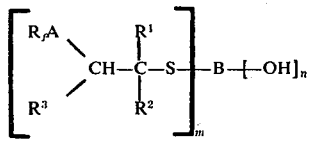

wherein $R^1$, $R^2$, $R^3$ are hydrogen, methyl, $R_fA$ or $R_fACH_2$ with the requirement at lease one of $R^1$, $R^2$, $R^3$ represent $R_fA$ or $R_fACH_2$;
$R_f$ is a perfluoroalkyl group of 1 to 18 carbon atoms;
$AR_f$ is

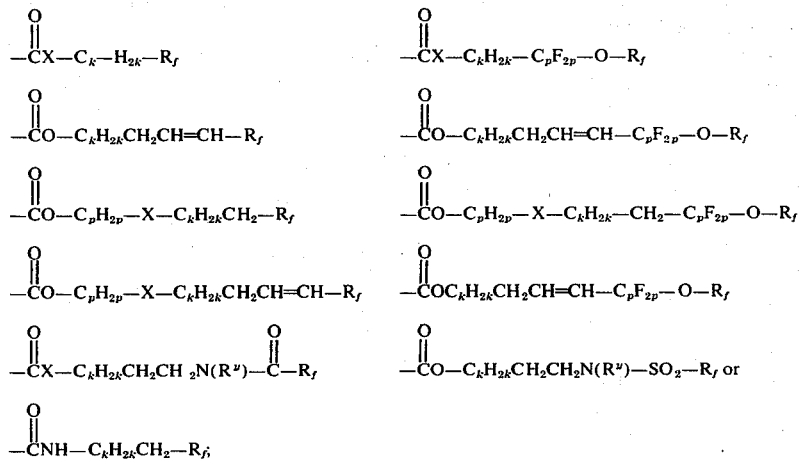

X is oxygen or sulfur;
$k$ is zero to 10;
$p$ is 2 to 12;
$R^y$ is hydrogen or alkyl of 1 to 4 carbon atoms;
$m$ is 1 to 6;
$n$ is 1 to 6;
and B is an inert linkage group.

In the above definition B is required to be an inert linkage group. Inert in the present context is employed in its normal definition so that B remains as a discrete unreacted group in the starting and final compound in the reaction procedure to produce the novel perfluoroalkyl ($R_f$) alcohol of formula I.

A suitable method for forming the novel $R_f$-alcohols of formula I, involves a base or free radical catalyzed addition reaction of $\alpha, \beta$-unsaturated di- or triesters of the formula:

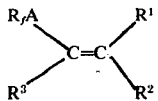

with
mono- or polymercaptoalcohols of formula:

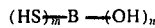

In formulas II and III the substituents have been defined previously in relationship to formula I.

The type of esters of formula II which may be employed are derived from fumaric, maleic, citraconic, mesaconic, itaconic, methylene malonic and aconitic acids. The formula II esters are defined to be:

| Type Ester | $R^1$ | $R^2$ | $R^3$ |
|---|---|---|---|
| Fumarate | —H | —$AR_f$ | —H |
| Maleate | —$AR_f$ | —H | —H |
| Mesaconate | —H | —$AR_f$ | —$CH_3$ |
| Citraconate | —$AR_f$ | —H | —$CH_3$ |
| Itaconate | —H | —H | —$CH_2AR_f$ |
| Methylene malonate | —H | —H | —$AR_f$ |
| cis-Aconitate | —H | —$AR_f$ | —$CH_2AR_f$ |
| trans-Aconitate | —$AR_f$ | —H | —$CH_2AR_f$ |

The preparation of perfluoroalkyl containing esters disclosed herein and especially useful in preparing the novel compounds or adducts of the present invention are described in the following copending applications assigned to the assignee of the present invention: Ser. No. 720,370 filed Apr. 10, 1968 now abandoned, in the names of Eduard K. Kleiner and Martin Knell; Ser. No. 732,040 filed May 27, 1968, in the names of Eduard K. Kleiner, Martin Knell and Pier Luigi Pacini now U.S. Pat. 3,658,857; Ser. No. 812,439, filed Apr. 1, 1969, in the name of Eduard K. Kleiner now U.S. Pat. No. 3,636,085; Ser. No. 820,647, filed Apr. 30, 1969, in the name of Eduard K. Kleiner now U.S. Pat. No. 3,658,843; and Ser. No. 833,706, filed June 16, 1969, in the names of Eduard K. Kleiner and Pier Luigi Pacini now U.S. Pat. No. 3,645,985; Ser. No. 199,793 filed on Nov. 11, 1971, in the names of Eduard K. Kleiner and Martin Knell which, as CIP application Ser. No. 299,487 issued as U.S. Pat. No. 3,763,116; and Ser. No. 199,794 filed on Nov. 11, 1971, in the names of Eduard K. Kleiner and Martin Knell now U.S. Pat. No. 3,794,623.

The disclosure of these copending applications for the preparation of the starting esters and the related subject matter is incorporated by reference herein.

Specifically disclosed from copending application Ser. No. 720,370 is the following: The monomer compounds of the present invention are of the following formula:

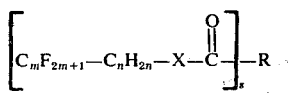

$$\left[ C_mF_{2m+1}-C_nH_{2n}-X-\overset{O}{\underset{\|}{C}}- \right]_s R \qquad \text{FORMULA I}$$

wherein
  m is an integer of 3 to 18, preferably 6 to 12, and most preferably 7 to 10;
  n is an integer of 0 to 10, preferably 1 or 2;
  X is oxygen or sulfur, preferably oxygen;
  R is an ethylenically unsaturated hydrocarbon radical derived from fumaric, maleic, citraconic, mesaconic, itaconic, aconitic, or methylene malonic acid, preferably fumaric; and
  s is an integer of 2 or 3 and is equal to the number of carboxyl groups of the acid from which R is derived, preferably being 2 to correspond to fumaric acid.

The ester monomers of this invention can generally be prepared by well known esterification reactions between: acids and perfluorinated alcohols, alkyl esters and perfluorinated alcohols, acid chloride and perfluorinated alcohols, acid salts and perfluorinated halogenides, and acid chlorides and perfluorinated alkoxides. Of course, it is understood that the corresponding mercaptans may be used in lieu of the alcohols.

Generally the reaction of acid chlorides with the perfluorinated alcohol or mercaptan is preferred since the acid chlorides are easily available and the esterification proceeds readily. An exception, of course, is the case of maleyl chloride and chloromaleyl chloride which do not exist.

The esterifications are carried out in the absence of a base.

The esters of methylene malonic acid generally require a two step synthesis. The intermediate malonesters are made using one of the above esterification techniques and then the methylene malonic ester is formed for example by condensation of the malonester with formaldehyde. See E. Haworth and W. H. Perkin, J. Chem. Soc. 73, 339 – 345 (1898).

Representative preparations of examples of alcohols and mercaptans useful as starting materials in the practice of this invention are disclosed in: U.S. Pat. Nos. 2,666,797; 3,283,012; 3,171,861; 3,285,975; 2,884,991; and French Pat. No. 1,221,415.

Other alcohols which may form esters with the above acids or derivatives thereof are those such as HO-(CH$_2$)$_n$CH=CH—R$_f$, disclosed in U.S. Pat. No. 3,285,975; HO—CH$_2$CH$_2$CF$_2$—O—R$_f$ disclosed in U.S. Pat. No. 2,826,564; and HO—(CH$_2$)$_n$O(CH$_2$)$_n$R$_f$ and HO(CH$_2$)$_n$S(CH$_2$)$_n$R$_f$ which are obtained by reduction of the corresponding CH$_3$OCO(CH$_2$)$_{n-6}$O(CH$_2$)$_m$R$_f$ esters described in U.S. Pat. No. 3,172,910.

The following examples describing certain representative embodiments of this invention will serve to further illustrate the nature of this invention. It is to be understood that the examples are merely illustrative and intended to enable those skilled in the art to practice the invention in all of the embodiments flowing therefrom and do not in anyway limit the scope of the invention defined in the claims. Unless otherwise specified, the relationship of parts by weight to parts by volume is that of grams to cubic centimeters, and temperatures are degrees Centigrade.

EXAMPLE 1 a. BIS(1,1-DIHYDROPERFLUOROBUTYL) FUMARATE

A mixture of 15.3 parts of fumaryl chloride and 40 parts of 1,1-dihydroperfluorobutyl alcohol is heated with stirring at 90° – 5° until no further hydrogen chloride is liberated. After a total reaction time of 120 hours, the product is isolated by distillaton. In this manner, 18.0 parts of bis (1,1-dihydroperfluorobutyl) fumarate boiling at 106° – 110° at 5 mm pressure and melting at 45° – 45.5° is obtained.

Analysis for C$_{12}$H$_6$F$_{14}$O$_4$
  Calculated: C, 30.01; H, 1.25
  Found: C, 29.92; H, 1.28 b. MIXED BIS (1,1,2,2-TETRAHYDROPERFLUOROALKYL) FUMARATE

The procedure of a) is repeated, using 120 parts of a mixture containing 42.0% C$_6$F$_{13}$CH$_2$CH$_2$OH, 35.8% C$_8$F$_{17}$CH$_2$CH$_2$OH, 21.0% C$_{10}$F$_{21}$CH$_2$CH$_2$OH, 1.0% C$_{12}$F$_{25}$CH$_2$CH$_2$OH and 0.2% C$_{14}$F$_{29}$CH$_2$CH$_2$OH instead of the 1,1-dihydroperfluorobutyl alcohol. After 5 hours of heating at 95° – 100°, VPC indicated that the reaction is essentially complete. Distillation of the product gives 93 parts of mixed fumarate diesters boiling at 145° – 207° at 0.020 mm. pressure and having the following microanalysis: C, 28.69; H, 1.05; F, 63.54.

EXAMPLE 2

BIS (1,1-DIHYDROPERFLUOROOCTYL) FUMARATE

A mixture of 57.5 parts of fumaryl chloride and 300 parts of 1,1-dihydroperfluorooctyl alcohol is heated with stirring at 80° – 5° until no further hydrogen chloride is liberated. The total reaction time is 141 hours. After two recrystallizations from isopropyl alcohol, 169.2 parts of bis (1,1-dihydroperfluorooctyl) fumarate, melting at 74° – 7° is obtained. Further purification yields material melting at 80° – 82.5° which is identified by microanalysis, IR and NMR spectroscopy.

EXAMPLE 3

BIS (1,1,2,2-TETRAHYDROPERFLUOROOOCTYL FUMARATE

A mixture of 9.46 parts of 1,1,2,2-tetrahydroperfluorooctanol (prepared as described in U.S. Pat. No. 3,283,012), 1.87 parts of dimethyl fumarate, 0.55 parts of concentrated sulfuric acid, and 100 parts by volume of toluene is placed in a pear shaped flask fitted with a short Vigreux distilling column. Toluene is distilled until no further methanol is detected in the distillate. Additional toluene is added as needed to the reaction flask during the reaction. On cooling, the product crystallizes from the toluene, and is filtered, and washed with water until the washings are neutral. After two recrystallizations from toluene and one from hexane, 1.4 parts of bis (1,1,2,2-tetrahydroperfluorooctyl) fumarate melting at 56° – 72° is obtained. Although the compound does not melt sharp, VPC, IR, NMR and microanalysis indicate that it is pure and has the desired structure.

Analysis for C$_{20}$H$_{10}$F$_{26}$O$_4$ -
  Calculated: C, 29.72; H, 1.25; F, 61.12
  Found: C, 29.53; H, 1.40; F, 60.76

EXAMPLE 4

BIS (1,1,2-2-TETRAHYDROPERFLUORONONYL) FUMARATE

A solution of 2.68 parts of fumaryl chloride and 14.5 parts of 1,1,2,2-tetrahydroperfluorononyl alcohol (prepared as described in U.S. Pat. No. 3,283,021) in 45.0 parts by volume of acetonitrile is allowed to stand overnight at room temperature. The reaction mixture is then heated with stirring at 80° for 3 hours. After cooling in an ice bath, the product is separated by filtration, washed with cold acetonitrile and air dried. 8.9 Parts of crude product are obtained. After two recrystallizations from isopropyl alcohol the melting point is 81° – 83.5° and the IR, NMR and microanalysis conform with the expected structure.

Analysis for $C_{22}H_{10}F_{30}O_4$ -
Calculated: C, 29.09; H, 1,11; F, 62.75
Found: C, 28.91; H, 1.24; F, 62,94

EXAMPLE 5

BIS (HEXAFLUOROISOPROPYL) FUMARATE

To a slurry of 2.4 parts of sodium hydride, as a 50% dispersion in mineral oil, in 45 parts of toluene, cooled to 15° is added with stirring 25.2 parts of hexafluoroisopropyl alcohol keeping the temperature below 30°. A solution of 7.7 parts of fumaryl chloride in 10 parts of toluene is then added dropwise with stirring keeping the temperature below 30°. The reaction mixture is stirred for 1½ hours at room temperature and heated to boiling. After cooling to room temperature, 100 parts of water is added. The toluene layer is separated, washed two times with 50 parts of water, dried over anhydrous magnesium sulfate, and distilled through an 18 inch spinning band column.

The product fraction, which boils at 66° at 4 mm pressure and melts at 53° – 5°, amounts to 13.6 parts and is identified by IR, NMR and microanalysis as bis (hexafluoroisopropyl) fumarate.

Analysis for $C_{10}H_4F_{12}O_4$ -
Calculated: C, 28,86; H, 0.97;
Found: C, 28.59: H, 0.96;

EXAMPLE 6

BIS (1,1,2,2-TETRAHYDROPERFLUORONONYLTHIOL) FUMARATE a. 1,1,2,2-Tetrahydroperfluorononyl mercaptan A mixture of 30.0 parts of 1,1,2,2-tetrahydroperfluorononyl iodide, 5.2 parts of thiourea and 150 parts by volume of ethanol is refluxed for 6 hours after which 12 parts of 25% sodium hydroxide solution is added dropwise with stirring and the resulting mixture refluxed for 1 hour. After cooling to room temperature, the reaction mixture is acidified with dilute sulfuric acid, 150 parts of water is added and the yellow organic layer is separated and dried over anhydrous magnesium sulfate. The product is then distilled through a short Vigreux column. In this manner, 13.7 parts of product boiling at 72° – 4° at 17 mm pressure is obtained. The product is identified as 1,1,2,2-tetrahydroperfluorononyl mercaptan by IR, NMR and microanalysis.

Analysis for $C_9H_5F_{15}S$ -
Calculated: C, 25.13; H, 1,17;
Found: C, 24.68; H, 1.29;

b. Bis (1,1,2,2-Tetrahydroperfluorononylthiolo) Fumarate

A mixture of 3.7 parts of 1,1,2,2-tetrahydroperfluorononyl mercaptan and 0.65 parts of fumaryl chloride is placed in a 10 ml. flask and heated at 80°C for 18 hours while passing a slow stream of nitrogen through the reaction flask. The resulting solid is dissolved in 7.0 parts by volume of α,α,α-trifluorotoluene and heated at 80° for an additional 3 hours. An additional 10 parts by volume of trifluorotoluene is added, the hot solution filtered, and the product allowed to crystallize slowly. After cooling, filtering, washing with cold trifluorotoluene, and drying, 0.85 parts of bis (1,1,2,2-tetrahydroperfluorononylthiolo) fumarate melting at 137.5° – 139° is obtained.

Analysis for $C_{22}H_{10}F_{30}S_2O_2$ -
Calculated: C, 28.03; H, 1.07;
Found: C, 27.98; H, 1.12;

EXAMPLE 7

BIS (1,1,2,2-TETRAHYDROPERFLUOROHEXYL) FUMARATE

A mixture of 5.05 parts of fumaryl chloride and 17.0 parts of 1,1,2,2-tetrahydroperfluorohexanol, prepared as described in U.S. Pat. No. 3,283,012, is heated with stirring at 80° – 90°C under a nitrogen atmosphere until the liberation of hydrogen chloride ceases and VPC indicates that the starting materials are no longer present. The crude reaction mixture is recrystallized from hot hexane yielding 12.3 parts of a colorless semi-solid. Further purification is carried out by dissolving in 1,1,2-trichloro-trifuloroethane, passing through a neutral aluminum oxide column and evaporating the solvent. The product is still a semi-solid at room temperature, but IR, NMR and VPC indicates that it is pure.

Analysis for $C_{16}H_{10}F_{18}O_4$ -
Calculated: C, 31.60; H, 1.66; F, 56.24
Found: C, 31.57; H, 1.65; F, 56.02

EXAMPLE 8

BIS (1.1-DIHYDROPERFLUOROOCTYL) ITACONATE

A mixture of 12.52 parts of itaconyl chloride and 72.52 parts of 1.1-dihydroperfluorooctyl alcohol and 50 parts of benzotrifuloride is refluxed for 72 hours. The benzotrifluoride is then removed on a rotary evaporator and the residue is distilled twice under high vacuum. 34.6 Parts (yield 47.4%) of pure bis (1.1-dihydroperfluorooctyl) itaconate, boiling point 120° – 131°C at 0.1 mm Hg. pressure is obtained. Identification is made by microanalysis, IR and NMR.

Analysis for $C_{21}H_6O_4F_{30}$ -
Calculated: C, 28.20; H, 0.90; F, 63,74
Found: C, 24,41; H, 1.18; F, 64.00

EXAMPLE 9

BIS (1.1-DIHYDROPERFLUOROOCTYL) MALONATE

A mixture of 14.8 parts of malonyl chloride, 84.02 parts of 1.1-dihydroperfluorooctyl alcohol and 200 parts of dry toluene was refluxed for 45 hours. The toluene was removed in a rotary evaporator and the residue was distilled under high vacuum. 37.54 parts (yield 86.5%) of pure bis (1.1-dihydroperfluorooctyl) malonate, boiling point 122° – 125° at 0.2 mm Hg. pressure is obtained. It is soluble at room temperature and melts at 35.5° – 36.5°C. Purity test and identification is made by VPC, IR and NMR.

Analysis for $C_{19}H_6F_{30}O_4$ -
Calculated: C, 26.28; H, 0.70; F, 65.65
Found: C, 26.14; H, 0.78; F, 65.32

EXAMPLE 10

BIS (1-METHYL-1,2,2-TRIHYDROPERFLUORONONYL) FUMARATE a. 1-Methyl-1,2,2-Trihydroperfluoronoyl nitrate To a solution of 18.7 parts of silver nitrate in 60 parts of acetonitrile is added dropwise with stirring 53.8 parts of 1-methyl-1,2,2-trihydroperfluorononyl iodide. The addition takes 50 minutes and there is no visible exotherm, but after a short time, a yellow solid begins to separate. Stirring is continued at room temperature for 72 hours, after which time the solid is removed by filtration. Water (100 parts) is added to the filtrate, the lower layer separated, dried over anhydrous magnesium sulfate, and distilled through an 18 inch spinning band column. In this manner, 32.5 parts of the desired 1-methyl-1,2,2-trihydroperfluorononyl nitrate, boiling at 77° – 70° at 4 mm pressure is obtained.

Analysis for $C_{10}H_6F_{15}NO_3$ -
Calculated: C, 25,38; H, 1.28; N, 3.03; F, 60.25
Found: C, 25.19; H, 1.32; N, 3,34; F. 60.07 b. 1-Methyl-1,2,2-Trihydroperfluorononyl

To a slurry of 44.7 parts of 60% sodium sulfhydrate in 100 parts by volume of ethanol is added dropwise in 1 hour 28.4 g of 1-methyl-1,2,2-trihydroperfluorononyl nitrate. The reaction is exothermic to 35°C. After stirring at room temperature for 1 hour, 250 parts of water is added, the bottom layer separated, washed again with water, and dried over anhydrous magnesium sulfate. Distillation through a short Vigreus column gives 20.5 parts of 1-methyl-1,2,2-trihydroperfluorononyl, boiling at 82°C at 100 mm. pressure.

Analysis for $C_{10}H_7F_{15}O$ -
Calculated: C, 28.05; H, 1.69; F, 66.56
Found: C, 28.15; H, 1.52; F, 66.35 c. Bis (1-Methyl-1,2,2-Trihydroperfluorononyl) Fumarate

A mixture of 15.0 parts of 1-methyl-1,2,2-trihydroperfluorononyl, 2.68 parts of fumaryl chloride and 15.0 parts of triglyme is heated with stirring at 95° – 100°C for 32 hours and at 125°C for 35 hours until the evolution of hydrogen chloride ceases. After cooling to room temperature, water is added and the product extracted into ether. The ether solution is washed with 10% sodium bicarbonate, water and then dried over anhydrous magnesium sulfate. After evaporation of solvent, the product is distilled through a micro distillation apparatus. Six and one half parts of the fraction boiling at 140° – 160°C at 0.050 mm pressure is obtained. This fraction analysed only 68% product by VPC, so it was recrystallized two times from hot ethanol. In this manner, 3.0 parts of bis (1-methyl-1,2,2-trihydroperfluorononyl) fumarate, which is 99+% pure by VPC, is obtained.

Analysis for $C_{24}H_{14}F_{30}O_4$ -
Calculated: C, 30.78; H, 1.51; F, 60.87
Found: C, 30.44; H, 1.81; F, 60.92

EXAMPLE 11

Using procedures of the foregoing examples employing stoichiometrically equivalent amounts of corresponding starting materials, the following compounds of FORMULA I are obtained.

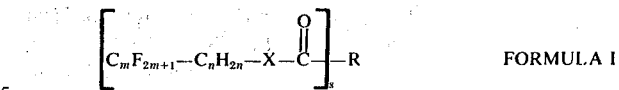

FORMULA I

| | $C_mF_{2m+1}$ | $C_nH_{2n}$ | X | S | R |
|---|---|---|---|---|---|
| 11a | $(CF_3)_2CF$ | $CH_2CH_2$ | O | 2 | from citraconic acid |
| 11b | $CF_3(CF_2)_6$ | $(CH_2)_{10}$ | O | 2 | from fumaric acid |
| 11c | $CF_3(CF_2)_6$ | $CH_2$ | S | 3 | from aconitic acid |
| 11d | $CF_3(CF_2)_{17}$ | $CH_2CH_2$ | O | 2 | from fumaric acid |
| 11e | $(CF_3)_2(CF_2)_4$ | $(CH_2)_4$ | S | 2 | from mesaconic acid |
| 11f | $CF_3(CF_2)_8$ | $CH_2$ | O | 2 | from maleic acid |

Mercaptoalcohols of type III

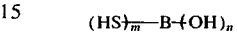

may contain from 1 to 6 hydroxy and mercapto groups and are either commercially available or can be easily prepared. Among the commercially available mercapto alcohols, the following are of special importance:

| | |
|---|---|
| 2-mercaptoethanol | $HSCH_2CH_2OH$ |
| 2,3-dimercapto-1-propanol | $HSCH_2CH(SH)CH_2OH$ |
| 3-mercapto-1,2-propanediol | $HSCH_2CH(OH)CH_2OH$ |
| 1,3-dimercapto-2-propanol | $HSCH_2CH(OH)CH_2SH$ |
| 1,4-dimercapto-2,3-butanediol | $HSCH_2CH(OH)CH(OH)CH_2SH$ |

Of importance also are mercaptoalcohols derived from polyols and thioglycolic acid or 3 mercaptopropionic acid, such as

| | |
|---|---|
| hydroxyethyl thioglycolate | $HSCH_2COOCH_2CH_2OH$ |
| hydroxyethyl mercaptopropionate | $HSCH_2CH_2COOCH_2CH_2OH$ |
| hydroxyalkyl thioglycolate | $HSCH_2COOC_nH_{2n}OH_n$ |
| hydroxyalkyl mercaptopropionate | $HSCH_2CH_2COOC_nH_{2n}OH_n$ |

Additionally suitable are thioglycolates and mercaptopropionates derived from mono, di- and tripentaerythritol and thioglycolic or mercaptopropionic acid:

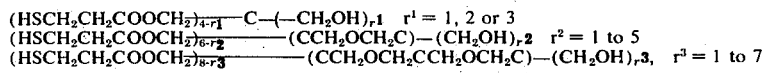

Of similar interest are mercaptoalcohols which are obtained by partially esterifying trimethylolethane, trimethylolpropane, polyhydroxy compounds such as sorbitol, with thioglycolic or mercaptopropionic acid.

Also suitable are mercapto alcohols known as Dion Polymercaptan Resins:

| | | |
|---|---|---|
| DPM 3-800LC | $R[O(C_3H_6O)_N CH_2CH(CH)CH_2SH]_3$ | $N = 1-2$ |
| DPM 1002 | $R[O(C_3H_6O)_{N^1}CH_2CH(OH)CH_2SH]_{N^2}$ | $N^1 = 20-25$ |
| DPM 5-1300 | $R[O(C_3H_6O)_{N^1}CH_2CH(OH)CH_2SH]_5$ | $N^2 = 2-3$ |

Referring to the starting mono or poly-mercaptoalcohols of formula III,

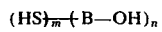

B serves as an inert linkage only and connects the mercapto and the hydroxy groups. The sole criticality for B is that it remains intact throughout the reaction.

The addition of mercaptoalcohols of type III to α, β-unsaturated di- and triesters of type II is accomplished either by a base or free radical catalysis.

The base catalyzed addition reaction of mercaptans to α, β-unsaturated esters is well known and described in detail in: Houben-Weyl, Methoden der Organischen Chemie, Volume 9, pages 123 to 126 (Georg Thieme Verlag, Stuttgart)

The preferred bases recommended for such addition reactions are generally strong inorganic or organic bases such as:

Sodium or potassium methoxide or ethoxide, benzyltrimethylammonium hydroxide, piperidine or pyridine. Generally these bases are employed in amounts from 0.01% to 2% at temperatures from room temperature to 100°C.

It has been found, however, that the mercaptoalcohols can be added to α,β-unsaturated di- and triesters of type III with very weak organic bases such as tertiary amines, as for instance:
- triethylamine
- N-methylmorpholine
- triethylenediamine
- N,N-dimethylpiperazine
- N-ethylmorpholine
- tetramethyl-1,4-butanediamine
- diethylcyclohexylamine
- dimethylethanolamine
- dimethylethylamine
- diethylmethylamine The use of such weak bases has many advantages, including the reduced formation of colored by-products, the possibility of leaving the weak base in the final product, the simplification of the work-up procedure with reduced costs, and little or no reaction occurs with solvents sensitive toward strong bases such as ketones or esters.

It is also possible to use free radical initiators or U.V. light for the addition of the mercaptans of type III to di- and triesters of type II. This is possible because the di- and triesters of type II are very reluctant toward homopolymerization in contrast to acrylic esters. A suitable catalyst may be any one of the commonly known agents for initiating the polymerization of vinyl monomers such as azo-initiators, (e.g. azobisisobutyronitrile) or aliphatic and aromatic acyl peroxides, e.g. decanoyl peroxide, lauroyl peroxide, benzoyl peroxide, dialkyl peroxides, e.g. t-butyl-peroxide, cumyl peroxide; or hydroperoxides, e.g. t-butylhydroperoxide, cumene hydroperoxide, or peresters and peroxycarbonates, e.g. t-butyl perbenzoate.

The use of base catalysis yields strictly adducts of formula I

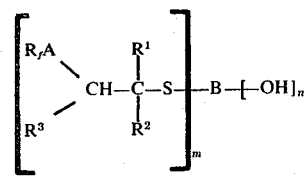

i.e. one α,β-unsaturated ester double bond reacts with one mercapto group. The use of free radical initiators on the other hand yields also mainly adducts of formula I above, due to the reluctance of the di- and triesters toward homopolymerization. However, it is unavoidable that a certain percentage of oligomers of formula IV are formed:

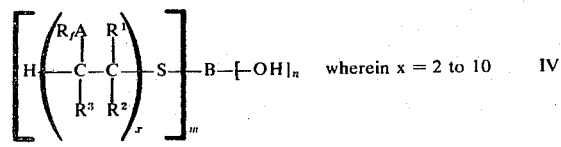 wherein x = 2 to 10    IV

It is for this reason that the use of base catalysis is preferred over the use of free radical catalysis.

The addition of the mercaptoalcohols to the di- and triesters of type II is usually carried out in a solvent in which the reactants and preferably also the adduct are soluble at the reaction temperature employed. Suitable solvents are aliphatic or aromatic hydrocarbons such as heptane, benzene, toluene, etc; chlorinated or fluorinated aliphatic or aromatic hydrocarbons such as methylene chloride, chloroform, methyl chloroform, carbon tetrachloride, trichloroethylene, perchloroethylene, Freon's such as 1,1,2-trifluoro-1,2,2-trichloroethane, etc., chlorobenzene, benzotrifluoride or hexafluoroxylene, ketones, esters and ethers such as acetone, methyl isobutyl ketone, ethyl acetate and high homologs, dialkyl ethers, tetrahydrofuran, ethylene glycol monomethyl or monoethyl ether, ethylene glycol dimethyl or diethyl ether, and mixtures of these ketones, esters or ethers with water.

The addition reaction is very simple to carry out, i.e. the mercaptan III and the di- or triester II are dissolved at the desired molar ratios in a solvent described above and the catalyst (0.01–2%) is added. The reaction mixture is kept at a temperature ranging from room temperature to 100°C, preferably under nitrogen until the disappearance of the double bond of the ester II indicates that the reaction is complete. Other means of following the reaction are GC (gas chromatography), titration of free mercapto groups or TLC (thin layer chromatography). Required reaction times depend on reaction temperatures and amounts and kind of catalysts employed and may range from 5 minutes to 24 hours. To obtain products free of discoloration, it is preferred to work at reaction temperatures below 70°C, and preferably 40° to 60°C. If required, the addition product can be isolated by evaporating the solvent and catalyst (low volatile catalysts such as triethylamine are preferred) and be purified employing crystallization, precipitation or distillation procedures.

The novel $R_f$- alcohols of type I are characterized by having two or three closely packed $R_f$-groups per reacted -SH group in the adduct molecule. This fact is most important since close packed pairs or triplets of $R_f$- groups in a molecule give considerable higher oil repellency ratings if compared with a molecule containing isolated $R_f$-groups, i.e. $R_f$-groups which are separated by one or more backbone carbons. For this reason it is most important that at least one of the substituents $R^1$, $R^2$ or $R^3$ in the esters of type II,

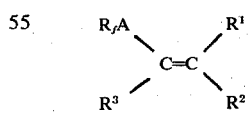

is $R_fA$ or $R_fACH_2$- as defined earlier.

With use of α,β-unsaturated esters where $R^1$, $R^2$, and $R^3$ are hydrogen or methyl, as is the case for perfluoroalkyl acrylates or methacrylates, formation of $R_f$- alcohols will yield polymers with considerably lower oil repellencies compared on an equal fluorine on fabric basis. Reaction (a) below illustrates formation of a more desirable alcohol due to closely spaced $R_f$ groups in comparison with reaction (b) forming an alcohol with only one $R_f$ group and no close spacing.

Since the novel alcohols may possess at times relatively small or no film forming properties, it is advanta-

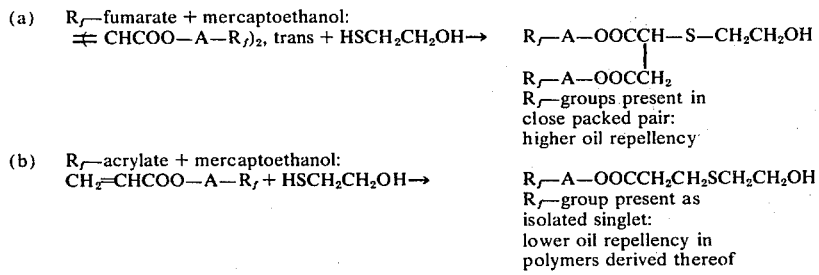

(a)  $R_f$—fumarate + mercaptoethanol:
 $\rightleftharpoons$ CHCOO—A—$R_f$)$_2$, trans + HSCH$_2$CH$_2$OH →

$R_f$—A—OOCCH—S—CH$_2$CH$_2$OH
|
$R_f$—A—OOCCH$_2$
$R_f$—groups present in close packed pair: higher oil repellency (b)  $R_f$—acrylate + mercaptoethanol:
CH$_2$=CHCOO—A—$R_f$ + HSCH$_2$CH$_2$OH →

$R_f$—A—OOCCH$_2$CH$_2$SCH$_2$CH$_2$OH
$R_f$—group present as isolated singlet: lower oil repellency in polymers derived thereof The novel $R_f$-alcohols of type I are useful in many ways: They are interesting intermediates for the synthesis of novel acrylates, methacrylates, fumarates and related α, β-unsaturated esters, which can be polymerized by free radicals to yield highly efficient soil repellent finishes for textiles, paper, leather and other substrates:

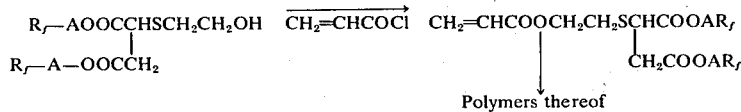

$R_f$—AOOCCHSCH$_2$CH$_2$OH $\xrightarrow{\text{CH}_2=\text{CHCOCl}}$ CH$_2$=CHCOOCH$_2$CH$_2$SCHCOOAR$_f$
|                                                                                    |
$R_f$—A—OOCCH$_2$                                                                    CH$_2$COOAR$_f$

↓

Polymers thereof

Novel $R_f$-alcohols having one or more hydroxy groups are useful intermediates for the synthesis of soil repellent polycondensation products which are obtained by reacting the $R_f$-alcohols with isocyanates.

The more complex and higher molecular weight $R_f$-alcohols of type I where m and n may range from 1 to 6 and especially $R_f$-alcohols of type I which are derived from Dion Polymercaptan resins or thioglycolates and mercaptopropionates derived from mono, di- and tripentaerythritol, are by themselves excellent soil repellent finished for textiles, paper, leather, wood, metallic surface and the like providing oil and water repellency to the treated substrates at extremely low add-ons.

The free hydroxy groups in these $R_f$-alcohols of type I are reactive sites able to react with crosslinking agents as well as with the substrate, which improves the fastness properties of the fluorochemical finish.

As shown in the examples, good repellency ratings are obtained with low fluorine contents of 0.08 to 0.12% by weight of the substrate. Besides oil and water repellency, the alcohols show excellent fastness properties such as wash and dryclean fastness, abrasion resistance and good drysoiling properties.

The novel alcohols may be applied to the various substrates by various coating techniques, such as dipping, spraying, brushing, padding, roll coating, and the like.

The alcohol of type I can be applied from a solvent and preferably from a solvent in which it was prepared for economical reasons.

The alcohol may also be applied from an aqueous system if either the application solution is water miscible or the solution has been postemulsified, by use of emulsifiers and emulsification techniques known in the art. It is understood that other finishes such as extenders, softeners, handbuilders, permanent press resins, catalysts and the like can be employed in the application system.

geous to apply the alcohol substrates in combination with film forming polymers or copolymers, as used for instance, for textile pigment printing and textile finishing in general. If the alcohol is applied from a solvent, then the polymeric extenders are dissolved in the same or a compatible solvent and coapplied to the substrate. In the case where a postemulsified adduct-solution is applied from an aqueous medium, the preferred extenders are aqueous polymer dispersions which are miscible with the post-emulsified adduct-solutions.

Polymers useful for such blends, include for example, but without limitation, polymers and copolymers of alkyl acrylates and alkyl methacrylates, such as methyl methacylate, ethyl methacrylate, isobutyl methacrylate, hexyl methacrylate, and n-octyl methacrylate. Particularly suitable polymers are poly(methyl methacrylate), poly(isobutyl methacrylate) and poly(n-octyl methacrylate). Also useful are polymers and copolymers of acrylic acid, methacrylic acid, styrene, alkyl styrene, butadiene, 2-methyl-1,3-butadiene, 2-chloro-1,3-butadiene; polymers and copolymers of vinyl esters such as vinyl acetate, vinyl butyrate, vinyl laurate, vinyl stearate, vinyl 2-ethylhexanoate; polymers and copolymers of vinyl halides and vinylidene halides, such as vinyl chloride, vinylidene chloride, vinyl fluoride, vinylidene fluoride; polymers and copolymers of allyl esters such as allyl propionate, or allyl caprylate; polymers and copolymers of vinyl ketones, such as vinyl methyl ketone, vinyl ethyl ketone, and the like; polymers and copolymers of vinyl ethers such as methyl vinyl ether, cetyl vinyl ether, and the like; polymers and copolymers of acrylamide, methacrylamide, N-methylol acrylamide, N-methylol methacrylamide, N-isopropyl acrylamide, diacetone acrylamide, hydroxymethyl diacetone acrylamide, acrylonitrile and methacrylonitrile.

For example, from about 20 to 97% by weight of poly(methyl methacrylate) blended with the polymer composition of this invention provides very useful coating compositions which retain surprisingly high repellency ratings even though the relative amount of fluorinated polymer is very low.

A preferred class of extender polymers for the $R_f$-alcohols of the present invention, particularly for textile applications, is disclosed in U.S. Pat. No. 3,349,054. These extender polymers give soft finishes that are light stable and help to impart excellent washand-dry clean fastness to finishes derived from adducts described in this invention.

Of course, it is understood that besides application to textiles, the coatings of the fluorinated polymer compositions of the present invention are useful in providing oil and water repellent coatings for leather, paper, wood, masonry, metals, plastics, glass, painted surfaces, and the like. A very significant advantage of the polymer compositions of the present invention is that they form effective oil repellent coatings at relatively very low fluorine levels on the substrate. In other words, on a given weight basis, the fluorine content of the polymer compositions of this invention exhibits more effective repellent properties than the same level of fluorine in other polymer compositions previously utilized in the art.

In the following section showing the synthesis of the novel compounds of this disclosure, the mercaptoalcohols are commercially available while the $R_f$-esters of type II are tabulated in Table I.

Table I

| Example | Name | $R_f$-esters of Type II employed for the synthesis of $R_f$-Alcohols Structure | Ref. |
|---|---|---|---|
| A | Bis(1,1-dihydroperfluorooctyl) fumarate, mp. 80–82.5°C | $\rightleftharpoons$ CHCOOCH$_2$C$_7$F$_{15}$)$_2$, trans, | Ser. No. 720,390 Ex. 2 |
| B | Bis(1,1,2,2-tetrahydroperfluorodecyl) fumarate, mp. 81–83.5°C | $\rightleftharpoons$ CHCOOCH$_2$CH$_2$C$_8$F$_{17}$)$_2$, trans | Ser. No. 720,370 |
| C | Bis(1,1,2,2-tetrahydroperfluoroalkyl) fumarate, see table I(b) | $\rightleftharpoons$ CHCOOCH$_2$CH$_2$R$_f$)$_2$, trans $R_f$= —C$_8$F$_{13}$, —C$_8$F$_{17}$, —C$_{10}$F$_{21}$, | Ser. No. 720,370 |
| D | Bis(1,1-dihydroperfluorooctyl) itaconate, bp. 128–131°C at 0.1mm | CH$_2$=C(CH$_2$COOCH$_2$C$_7$F$_{15}$)— COOCH$_2$C$_7$F$_{15}$ | Ser. No. 720,370 Ex. 8 |
| E | Bis(1,1,2,2-tetrahydroperfluorononyl) thiofumarate mp. 137.5–139°C | $\rightleftharpoons$ CHCOSCH$_2$CH$_2$C$_7$F$_{15}$)$_2$, trans | Ser. No. 720,370 Ex. 6 |
| F | Bis[4-(perfluoroheptyl)-3-butenyl] fumarate, bp. 182° at 0.4mm | $\rightleftharpoons$ CHCOOCH$_2$CH$_2$CH=CHC$_7$F$_{15}$)$_2$, trans | CIP/GC 309 FCR-27 |
| G | Bis[6-(perfluoroheptyl)-3-oxa-5-hexenyl] itaconate, bp. 208–216 at 0.8mm | CH$_2$=CCOOCH$_2$CH$_2$OCH$_2$CH=CHC$_7$F$_{15}$<br>CH$_2$COOCH$_2$CH$_2$OCH$_2$CH=CHC$_7$F$_{15}$ | CIP/GC 309 FCR-27 |
| H | Bis[6-perfluorooctyl)-4-thiahexyl] fumarate, mp. 81–83°C | $\rightleftharpoons$ CHCOOCH$_2$CH$_2$CH$_2$SCH$_2$CH$_2$C$_8$F$_{17}$)$_2$, trans | CIP/GC 309 FCR-26 |
| I | Bis(4-perfluoroisopropoxy-1,1,2,2-tetrahydroperfluorobutyl) fumarate, bp. 110°C at 0.2mm | $\rightleftharpoons$ CHCOOCH$_2$CH$_2$CF$_2$CF$_2$OCF(CF$_3$)$_2$]$_2$, trans | CIP/GC 309 FCR-27 |
| J | Bis[2-(n-perfluorooctanamido)ethyl] fumarate, mp. 151–152.5°C | $\rightleftharpoons$ CHCOOCH$_2$CH$_2$NHCOC$_7$F$_{15}$)$_2$, trans | Ser. No. 732,040 Ex. 1 |
|  | Bis[2-(N-ethyl-n-perfluorooctanesulfonamido)ethyl] itaconite m.p. 99.5–100.5°C | CH$_2$=CCOOCH$_2$CH$_2$N(C$_2$H$_5$)SO$_2$C$_8$F$_{17}$<br>CH$_2$COOCH$_2$CH$_2$N(C$_2$H$_5$)SO$_2$C$_8$F$_{17}$ | Ser. No. 812,439 Ex. 5 |
|  | Bis[2-(N-ethyl-n-perfluorooctanesulfonamido)ethyl] fumarate m.p. 112–112.5°C | $\rightleftharpoons$ CHCOOCH$_2$CH$_2$N(C$_2$H$_5$)SO$_2$C$_8$F$_{17}$]$_2$, trans | Ser. No. 812,439 Ex. 1 |
|  | Bis(N-1,1-dihydroperfluorooctyl) itaconamide, mp. 142–143°C | CH$_2$=CCONCH$_2$C$_7$F$_{15}$<br>CH$_2$CONCH$_2$C$_7$F$_{15}$ | Ser. No. 820,647 Ex. 5 |
|  | Bis(1,1-dihydrotrifluoroethyl) fumarate | $\rightleftharpoons$ CHCOOCH$_2$CF$_3$]$_2$, trans |  |
|  | Bis(1-hydrohexafluoroisopropyl) fumarate | $\rightleftharpoons$ CHCOOCH(CF$_3$)$_2$]$_2$, trans | Serial No. 720,370 |

Table I-b Composition and Analysis of $R_f$-fumarate Example C

The $R_f$-fumarate mixture of the type $\rightleftharpoons$CHCOOCH$_2$CH$_2$R$_f$)$_2$, trans, derived from a mixture of $R_f$CH$_2$CH$_2$I, where $R_f$= —C$_6$F$_{13}$, —C$_8$F$_{17}$ and —C$_{10}$F$_{21}$, is an off-white wax, and has the following composition according to GC analysis:

Diester-Content:
$C_{12}$—diester: 3.5% (= —C$_6$F$_{13}$ + —C$_6$F$_{13}$)
$C_{14}$—diester: 21.7% (= —C$_6$F$_{13}$ + C$_8$F$_{17}$)
$C_{16}$—diester: 38.8% (= —C$_6$F$_{13}$ + —C$_{10}$F$_{21}$ and
$C_{18}$—diester: 27.6% (= —C$_8$F$_{17}$ + C$_{10}$F$_{21}$)
$C_{20}$—diester: 8.0% (= —C$_{10}$F$_{21}$ + —C$_{10}$F$_{21}$)
Unknowns: 0.4%

Average Mol. Weight: 987.3
Fluorine Content: 63.91%
Boiling Range: 150 to 220°C at 0.01 mm Hg
Melting Range: 66 to 75°C

EXAMPLE 1

2-[1,2-Bis(1,1,2,2-tetrahydroperfluorodecoxycarbonyl) ethylthio]ethanol

C$_8$F$_{17}$CH$_2$CH$_2$OOCCHSCH$_2$CH$_2$OH
|
C$_8$F$_{17}$CH$_2$CH$_2$OOCCH$_2$

Bis(1,1,2,2-tetrahydroperfluorodecyl) fumarate (5.04g, 0.005 mole, Example B), 2-mercaptoethanol (0.390g, 0.005 mole), triethylamine (0.10g) and methyl chloroform (15g) were sealed in an ampul under nitrogen. The ampul was heated at 60°C for 16 hours. On cooling, a precipitate formed; this was filtered and recrystallized from carbon tetrachloride to which a small amount of chloroform had been added. The product was obtained as white crystals (mp 675°–68°C) in a 61% yield (3.3g). The NMR showed proton resonances at δ 1.9–3.2, 9 protons is unresolved overlapping multiplets, HOCH$_2$CH$_2$SCH(CH$_2$COOCH$_2$CH$_2$C$_8$F$_{17}$)COOCH$_2$CH$_2$C$_8$F$_{17}$; δ 3.1–4.0, 3 protons in a triplet and a doublet of doublets, HO$\underline{CH_2}$CH$_2$S$\underline{CH}$CH$_2$; δ 4.45, 4 protons in overlapping triplets, (COOCH$_2$CH$_2$)× 2. These data are consistent for the structure.

Analysis for C$_{26}$H$_{16}$F$_{34}$O$_5$S:
  Calc.: C, 28.74; H, 1.48; F, 59.46;
  Found: C, 28.76; H, 1.52; F, 60.14

EXAMPLE 2

2-[1,2-Bis(1,1,2,2-tetrahydroperfluoroalkoxycarbonyl)-ethylthio]ethanol

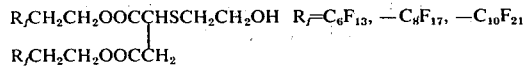

Bis(1,1,2,2-tetrahydroperfluoroalkyl) fumarate (300 g, 0.297 mole, Example C), 2-mercaptoethanol (24.3g, 0.311 mole), triethylamine (3.0g) were dissolved in 3000 ml of acetone and kept for four hours under nitrogen at 45°C, after which time the acetone was evaporated and the crude adduct obtained as a viscous oil. The oil was dissolved in 300 ml of chloroform at 40°C, filtered through cotton fibers and precipitated under vigorous stirring into 3000 ml of heptane. The product precipitated as a granular wax which was filtered off and triturated three times with 200 ml of heptane. After drying, the product was obtained as an off-white, granular wax, weighing 257.8g (79.8% of theory), having a m.p. of 58°–67°C. The proton NMR showed resonances as recorded in Example 1, confirming the above structure.

Analysis Found: C, 28.99; H, 1.15; F, 58.69

EXAMPLE 3

1,3-Bis[1,2-bis(1,1,2,2-tetrahydroperfluorodecoxycarbonyl)ethylthio]-2-propanol

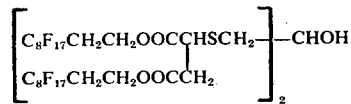

Bis(1,1,2,2-tetrahydroperfluorodecyl) fumarate (24.2g, 0.024 mole, Example B), 1,3-dimercapto-2-propanol (1.49g, 0.012 mole), triethylamine (0.25g) and 75g of methyl chloroform were charged in a reaction flask and kept at 65°C for 26 hours after which time the reaction was completed based on IR-analysis (disappearance of fumarate double bond at 1300 cm$^{-1}$). After cooling of the reaction mixture, a precipitate was filtered and recrystallized from chloroform yielding 22.5g (87.8% yield) of a white powder with a m.p. of 78.5°–80°C. The NMR showed proton resonances at γ 2.0–3.5, 17 protons, 4x R$_f$CH$_2$—, + 2x—COCH$_2$— + 2x—SCH$_2$—+OH; γ 3.5–4.9, 11 protons, 4x—OCH$_2$— + 2x—SCH— + —OCH—. These data are consistent with the above structure.

Analysis for C$_{51}$H$_{28}$F$_{68}$O$_9$S$_2$:
  Calc.: C, 28.61; H, 1.32; F, 60.35
  Found: C, 28.93; H, 1.39; F, 61.07

EXAMPLE 4

2-[1,2-Bis[2-(N-ethyl-n-perfluorooctansulfonamidoethoxycarbonyl]ethylthio]ethanol

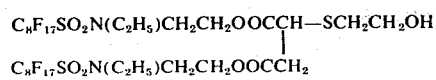

Bis[2-(N-ethyl-n-perfluorooctanesulfonamido)ethyl] fumarate (12.22g, 0.01 mole, Example 1), 2-mercaptoethanol (0.86g, 0.011 mole), triethylamine (0.13g) and 50g of methyl chloroform were charged into a reaction flask and kept at 65°C for 18 hours, after which time the reaction was complete according to IR-analysis. After evaporation of the solvent, the crude product was obtained as a viscous oil which was redissolved in acetone. The acetone solution was passed through 10g of neutral aluminum oxide, evaporated and again a very high viscous, tan oil was obtained, 13.0g (~100% yield) which could not be crystallized. The NMR showed proton resonances at δ 1.31, 6 protons, 2x—CH$_3$; δ 2.6 to 4.6, 20 remaining protons, including —OH. This spectrum is consistant with the above structure:

Analysis for C$_{30}$H$_{26}$F$_{14}$N$_2$O$_9$S$_3$
  Calc.: C, 27.70; H, 2.02; N, 2.15; F, 49.67
  Found: C, 27.80; H, 2.14; N, 2.21; F, 48.54

EXAMPLE 5

3-[1,2-Bis(1,1,2,2-tetrahydroperfluorodecoxycarbonyl)-ethylthio]-1,2-propanediol

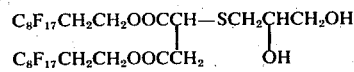

Bis(1,1,2,2-tetrahydroperfluorodecyl) fumarate (10.08g, 0.01 mole, Example B), 3-mercapto-1, 2-propanediol (1.08g, 0.105 mole), triethylamine (0.1g) and 44g of methyl chloroform were charged in a reaction flask and kept for 10 hours at 60°C after which time the reaction was completed according to IR analysis. On cooling the reaction mixture, the product crystallized, was filtered and recrystallized from chloroform yielding 9.5g (85% yield) of a white powder with a m.p. of 134°–135°C. The NMR showed proton resonances at δ 2.7; 8 protons, 2x R$_f$CH$_2$— + —SCH$_2$— + COCH$_2$—; δ 3.7, 6 protons, 2x —OH, + —OCH$_2$-CH—O + SCHCO; δ 4.5, 4 protons, 2x —COOCH$_2$—. This spectrum is consistent for the above structure.

Analysis for C$_{27}$H$_{18}$F$_{34}$O$_6$S:
  Calc.: C, 29.04; H, 1.62; F, 57.86
  Found: C, 29.13; H, 1.66; F, 57.02

EXAMPLE 6

3-[1,2-Bis(1,1,2,2-tetrahydroperfluoroalkoxycarbonyl)-ethylthio]-1,2-propanediol

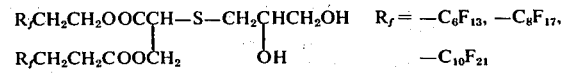

Bis(1,1,2,2-tetrahydroperfluoroalkyl) fumarate (300g, 0.297 mole, Example C), 3-mercapto-1,2-propanediol (33.6g, 0.311 mole), triethylamine (3.0g) and 3000 ml of acetone were charged into a reaction flask and stirred under nitrogen at 45°C for 4 hours, after which time the solvent was evaporated. A crude product was obtained as a viscous, frothy oil. The oil was dissolved in 300 ml of chloroform at 35°–40°C and after filtration of the warm solution through cotton fibers, the filtrate was stirred into 3000 ml of heptane. The product precipitated as a granular wax which was filtered, triturated 3 times with 200 ml of heptane and dried, yielding 297.2g (89.4% of theory) of an off-white wax having a melting range of 68°–120°C. The NMR spectrum showed identical hydrogen proton resonances as the C$_8$F$_{17}$— analogous compound (Example 5,) confirming the structure of above compound.

Analysis Found: C, 29.20; H, 1.89; F, 56.43

EXAMPLE 7

1,4-Bis[1,2-bis(1,1,2,2-tetrahydroperfluorodecoxycarbonyl)ethylthio]-2,3-butanediol

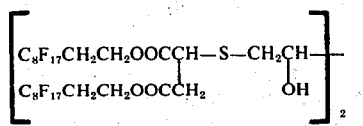

Bis(1,1,2,2-tetrahydroperfluorodecyl) fumarate (5.04g, 0.005 mole, Example B), 1,4-dimercapto-2,3-butanediol (0.385g, 0.0025 mole), triethylamine (0.05g) and 20ml of methyl chloroform were charged into a reaction flask and kept under nitrogen at 55°C for 4 hours after which time the reaction was completed (No fumarate double bond in IR at 1300 cm$^{-1}$ and —SH number zero). The product crystallized upon cooling and was filtered. Recrystallization from chloroform yielded 4.2g (88.5% yield) of a white powder with a m.p. of 124°–125°C. The NMR shows proton resonances at δ 2.3–3.4, 18 protons, 2x —OH +2x —SCH$_2$— + 4x R$_f$CH$_2$— + 2x —COCH$_2$—; δ 3.8, 4 protons, 2x —OCH-CH$_2$—SCH—; δ 4.5, 8 protons, 4x —OCH$_2$—, confirming the above structure.

Analysis for C$_{52}$H$_{30}$F$_{68}$O$_{10}$S$_2$:
Calc.: C, 28.77; H, 1.39; F, 59.51
Found: C, 28.86; H, 1.27; F, 60.91

EXAMPLE 8

1,4-Bis[1,2-bis(1,1,2,2-tetrahydroperfluoroalkoxycarbonyl)ethylthio]-2,3-butanediol

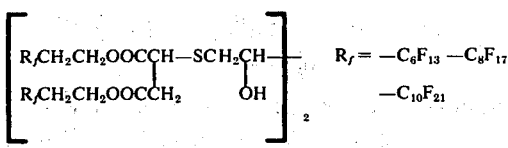

Bis(1,1,2,2-tetrahydroperfluoroalkyl) fumarate (10.1g, 0.01 mole, Example C), 1,4-dimercapto-2,3-butanediol (0.77g, 0.005 mole), triethylamine (0.1g) and 40g of methyl chloroform were reacted and the reaction product worked as described in Example 7. A total of 9.3g (88.5% yield) of a white powder with a m.p. of 90°–96°C was obtained, having an NMR proton resonance spectrum identical with the C$_8$F$_{17}$— analogue compound described in Example 7.

Analysis Found: F, 58.40

EXAMPLE 9

2-Hydroxyethyl 3-[1,2-bis(1,1,2,2-tetrahydroperfluorodecoxycarbonyl)ethylthio]propionate

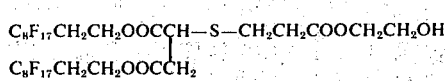

Bis(1,1,2,2-tetrahydroperfluorodecyl) fumarate (10.08g, 0.01 mole, Example B), hydroxyethyl mercaptopropionate (1.8g, 0.012 mole), triethylamine (0.06g) and 50g of methyl chloroform were sealed in an ampul and kept in a water bath shaker for 24 hours at 65°C. The solvent in the reaction mixture was evaporated and the residue twice crystallized from carbon tetrachloride yielding 10g of product containing trace amount of impurities according to TLC analysis. The 10g of product were dissolved in chloroform and passed through a column containing 30g of neutral aluminum oxide. A total of 4.9g of product containing no impurities (45.5% yield) were obtained, having a m.p. of 60°–63°C, while another 5g of product possessed trace impurities. The NMR of the pure product showed proton resonances at γ 2.0–3.3, 10 protons, 2x —COCH$_2$+ —SCH$_2$— + 2x R$_f$CH$_2$—; γ 3.28, 1 proton, —SCH—; γ 4.38, 8 protons, 4x —OCH$_2$—, while the —OH is lost in the base line. This NMR is consistent for above structure.

Analysis for C$_{29}$H$_{20}$F$_{34}$O$_7$S:
Calc.: C, 30.06; H, 1.74; F, 55.76
Found: C, 30.09; H, 1.59; F, 56.19

EXAMPLE 10

Adduct of bis(1,1,2,2-tetrahydroperfluoroalkyl) fumarate and Dion Brand Polymercaptan DPM-3-800-LC

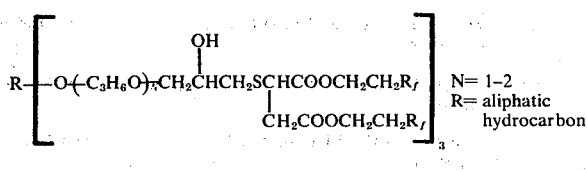

Bis(1,1,2,2-tetrahydroperfluroalkyl) fumarate (30.30g., 0.03 mole or 30 Meq. Example B) Dion Brand Polymercaptan DPM-3-800-LC (9.06, 30 Meq.), triethylamine (0.3g) and trichloroethane (118g) were charged into a flask and then heated at 50°C, under nitrogen, for 20 hours. An IR scan showed that the fumarate had been consumed (no absorbance at 1310 cm$^{-1}$ due to the fumarate double bond was observed). Titration for mercaptan with iodine solution showed that no mercaptan was present. The clear yellow solution was evaporated and a soft wax was obtained.

Analysis:
Calculated: F, 47.9
Found: F, 46.77

EXAMPLE 11

Adduct of bis(1,1,2,2-tetrahydroperfluoroalkyl) fumarate and Dion Brand Polymercaptan DPM-1002

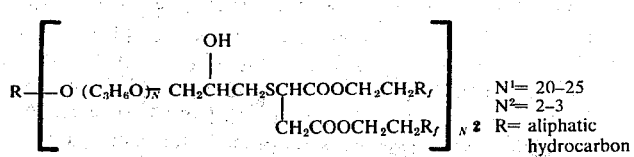

Bis(1,1,2,2-tetrahydroperfluoroalkyl) fumarate (10.10g, 0.01 mole or 10 Meq. Example B) Dion Brand Polymercaptan DPM - 1002 (39.0g, 10 Meq.), triethylamine (0.1g) and trichloroethane (147g) were charged into a flask and heated at 50°C, under nitrogen. The progress of the reaction was followed by IR analysis for the disappearance of the fumarate, and by titration for mercaptan. After 100 hours of heating, complete reaction was indicated by both methods. The clear solution was evaporated and a clear, very viscous oil was obtained.

Analysis:
Calculated: F, 12.8
Found: F, 11.62

EXAMPLE 12

Adduct of bis(1,1,2,2-tetrahydroperfluoroalkyl) fumarate and Dion Brand Polymercaptan DPM - 5 - 1300

EXAMPLES 13 – 23

Novel $R_f$-alcohols of Type I are prepared by reacting $\alpha,\beta$-unsaturated esters of Type II with mercapto-alcohols of Type III as listed in Table II, employing reaction conditions and work-up procedures as described in Examples 1 – 9.

EXAMPLES 24 – 26

25% solutions of the adducts of example 10, 11 and 12 in methyl chloroform were diluted with methyl chloroform and applied to a cotton print test fabric by a

TABLE II

| EX. | ESTER OF TYPE II | + | MERCAPTOALCOHOL OF TYPE III | → | $R_f$-ALCOHOL OF TYPE I |
|---|---|---|---|---|---|
| 13 | $2 \neq CHCOOCH_2C_7F_{15})_2$ Example A | + | $C\begin{matrix}(CH_2OOCCH_2CH_2SH)_2\\(CH_2OH)_2\end{matrix}$ | → | $\begin{bmatrix}C_7F_{15}CH_2OOCCH-S-CH_2CH_2COOCH_2\\C_7F_{15}CH_2OOCCH_2\end{bmatrix}_2 C(CH_2OH)_2$ |
| 14 | $CH_2=\overset{|}{C}COOCH_2C_7F_{15}$<br>$\overset{|}{C}H_2COOCH_2C_7F_{15}$<br>Example D | + | $HSCH_2COOCH_2CH_2OH$ | → | $C_7F_{15}CH_2OOCCH-S-CH_2COOCH_2CH_2OH$<br>$C_7F_{15}CH_2OOCCH_2$ |
| 15 | $2\neq CHCOSCH_2CH_2C_7F_{15})_2$ Example E | + | $HSCH_2CH(OH)CH_2SH$ | → | $\begin{bmatrix}C_7F_{15}CH_2CH_2SOCCH-SCH_2\\C_7F_{15}CH_2CH_2SOCCH_2\end{bmatrix}_2 CHOH$ |
| 16 | $\neq CHCOOCH_2CH_2CH=CHC_7F_{15})_2$ Example F | + | $HS-(CH_2)_{12}-OH$ | → | $C_7F_{15}CH=CHCH_2CH_2OOCCH-S-(CH_2)_{12}-OH$<br>$C_7F_{15}CH=CHCH_2CH_2OOCCH_2$ |
| 17 | $2\neq CHCOOCH_2CH_2CH_2SCH_2CH_2C_8F_{17})_2$ Example H | + | $(HSCH_2CH)_2^-$<br>$\overset{|}{OH}$ | → | $\begin{bmatrix}C_8F_{17}CH_2CH_2SCH_2CH_2CH_2OOCCH-SCH_2CH\\C_8F_{17}CH_2CH_2SCH_2CH_2CH_2OOCCH_2\;\;\;\overset{|}{OH}\end{bmatrix}_2$ |
| 18 | $\neq CHCOOCH_2CH_2CF_2CF_2OCF(CF_3)_2]_2$ Example I | + | $HSCH_2CH_2OH$ | → | $(CF_3)_2CFOCF_2CF_2CH_2CH_2OOCCH-S-CH_2CH_2OH$<br>$(CF_3)_2CFOCF_2CF_2CH_2CH_2OOCCH_2$ |
| 19 | $\neq CHCOOCH_2CH_2NHCOC_7F_{15})_2$ Example J | + | $HSCH_2CH(OH)CH_2OH$ | → | $C_7F_{15}CONHCH_2CH_2OOCCH-SCH_2CH(OH)CH_2OH$<br>$C_7F_{15}CONHCH_2CH_2OOCCH_2$ |
| 20 | $CH_2=\overset{|}{C}HCOOCH_2CH_2N(C_2H_5)SO_2C_8F_{17}$<br>$\overset{|}{C}H_2COOCH_2CH_2N(C_2H_5)SO_2C_8F_{17}$<br>Example K | + | $HS(CH_2)_6OH$ | → | $C_8F_{17}SO_2N(C_2H_5)CH_2CH_2OOCCHCH_2-S(CH_2)_6OH$<br>$C_8F_{17}SO_2N(C_2H_5)CH_2CH_2OOCCH_2$ |
| 21 | $CH_2=\overset{|}{C}CONHCH_2C_7F_{15}$<br>$\overset{|}{C}H_2CONHCH_2C_7F_{15}$<br>Example M | + | $HSCH_2CH_2OH$ | → | $C_7F_{15}CH_2NHOCCHCH_2-S-CH_2CH_2OH$<br>$C_7F_{15}CH_2NHOCCH_2$ |
| 22 | $2\neq CHCOOCH_2CF_3)_2$ Example N | + | $HSCH_2CH(SH)CH_2OH$ | → | $CF_3CH_2OOCCH-SCH_2CH-\!-\!-S-\!-\!-CHCOOCH_2CF_3$<br>$CF_3CH_2OOCCH_2\;\;\;\;CH_2OH\;\;\;\;CH_2COOCH_2CF_3$ |
| 23 | $2\neq CHCOOCH(CF_3)_2]_2$ Example O | + | $(HSCH_2CH)_2^-$<br>$\overset{|}{OH}$ | → | $\begin{bmatrix}(CF_3)_2CHOOCCH-S-CH_2CH\\(CF_3)_2CHOOCCH_2\;\;\;\;\;\overset{|}{OH}\end{bmatrix}_2$ |

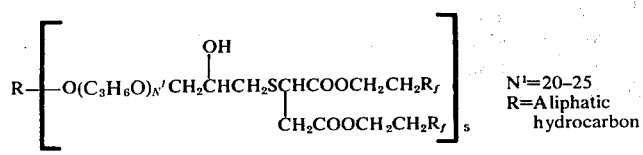

$N^1 = 20$–$25$
R = Aliphatic hydrocarbon

Bis(1,1,2,2-tetrahydroperfluoroalkyl) fumarate (30.30g., 0.03 mole or 30 Meq. Example B), Dion Brand Polymercaptan DPM-5-1300 (9.20g, 30 Meq.) triethylamine (0.3g) and trichloroethane (118.5g) were charged into a flask and then heated at 50°C, under nitrogen, for 20 hours. According to IR analysis, all fumarate had been consumed. Titration for mercaptan, with iodine reagent, showed that no mercaptan was present. The clear solution was evaporated leaving a soft foamlike material.

Analysis:
Calc.: F, 47.7
Found: F, 46.54 padding process in such a way to leave 0.12% fluorine deposited on the fabric. The fabric was evaluated after drying in a hot air oven at 150°C for 3 minutes.

The AATCC water spray test rating was determined according to Standard Test Method 22-1966 of the American Association of Textile Chemists and Colorists. Ratings are given from 50 (minimum) to 100 (maximum).

The AATCC Oil Rating was determined according to Standard Test Method 118-1966T of the American Association of Textile Chemists and Colorists. Ratings are given from 1 (minimum) to 8 (maximum). A commonly accepted level on soil repellent fabrics in the U.S. is an oil repellency of 3 – 4.

The ratings obtained with the adducts of examples 10, 11 and 12 are shown in Table III.

TABLE III

| EXAMPLE | ADDUCT EXAMPLE | AATCC OIL REPELLENCY | | AATCC WATER REPELLENCY | |
|---|---|---|---|---|---|
| | | 0.08% F | 0.12% F | 0.08% F | 0.12% F |
| 24 | 10 | 3 – 4 | 4 – 5 | 0 | 50 |
| 25 | 11 | 0 | 1 | 50 | 50 |
| 26 | 12 | 3 – 4 | 4 | 0 | 50 |

What is claimed is:
1. An alcohol of the formula

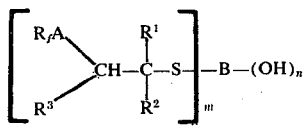

wherein
$R^1$, $R^2$ and $R^3$ are hydrogen, methyl, $R_fA$ or $R_fACH_2$ and at least one of $R^1$, $R^2$ and $R^3$ is $R_fA$ or $R_fACH_2$;
$R_f$ is a perfluoroalkyl group of 1 to 10 carbon atoms;
$R_fA$ is

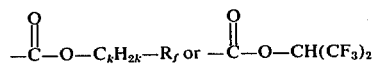

$k$ is 1 or 2;
$m$ is 1 or 2;
$n$ is 1 or 2;
and
B is saturated acyclic hydrocarbyl of 2 to 4 carbon atoms.

2. An alcohol of claim 1, wherein $R_fA$ is $-C(=O)O-C_kH_{2k}-R_f$, and $R_f$ is a perfluoroalkyl group of 6 to 10 carbon atoms.

3. An alcohol of claim 2, wherein $R^2$ and $R^3$ are hydrogen,
$R^1$ is $R_fA$,
$k$ is 2,
B is $-CH_2CH_2-$

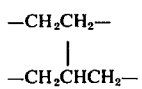

or

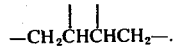

4. An alcohol of claim 2, wherein
$m$ is 1,
$n$ is 2, and

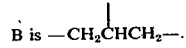

5. An alcohol of claim 2, wherein
$m$ is 1,
$n$ is 1, and
B is $-CH_2CH_2-$.

6. An alcohol of claim 2, wherein
$m$ is 2,
$n$ is 2, and

* * * * *